(12) United States Patent
Weber (10) Patent No.: US 8,119,153 B2
(45) Date of Patent: Feb. 21, 2012

(54) STENTS WITH DRUG ELUTING COATINGS (75) Inventor: Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2440 days.

(21) Appl. No.: 10/928,999

(22) Filed: Aug. 26, 2004

(65) Prior Publication Data
US 2006/0045901 A1 Mar. 2, 2006

(51) Int. Cl.
A61F 2/00 (2006.01)
(52) U.S. Cl. ....................................... 424/426
(58) Field of Classification Search .................. None
See application file for complete search history.

(56) References Cited

U.S. PATENT DOCUMENTS

| | | | |
|---|---|---|---|
| 5,899,935 A | 5/1999 | Ding | |
| 5,981,568 A | 11/1999 | Kunz et al. | |
| 5,993,972 A | 11/1999 | Reich et al. | |
| 6,005,020 A | 12/1999 | Loomis | |
| 6,007,845 A | 12/1999 | Domb et al. | |
| 6,013,855 A * | 1/2000 | McPherson et al. | 623/23.76 |
| 6,099,561 A | 8/2000 | Alt | |
| 6,174,329 B1 | 1/2001 | Callol et al. | |
| 6,179,817 B1 | 1/2001 | Zhong | |
| 6,193,951 B1 * | 2/2001 | Ottoboni et al. | 424/9.5 |
| 6,248,363 B1 | 6/2001 | Patel et al. | |
| 6,258,121 B1 | 7/2001 | Yang et al. | |
| 6,294,202 B1 * | 9/2001 | Burns et al. | 424/488 |
| 6,316,024 B1 | 11/2001 | Allen et al. | |
| 6,322,817 B1 | 11/2001 | Maitra et al. | |
| 6,368,658 B1 | 4/2002 | Schwarz et al. | |
| 7,056,550 B2 * | 6/2006 | Davila et al. | 427/2.24 |
| 2002/0010462 A1 | 1/2002 | Altman | |
| 2002/0013298 A1 | 1/2002 | Hunter | |

(Continued)

FOREIGN PATENT DOCUMENTS

WO WO 95/08320 3/1995

(Continued)

OTHER PUBLICATIONS

Luo et al. Novel biomaterials for drug delivery. Expert Opinion. Ther. Patents. 2001; 11(9):1395-1410.*

(Continued)

Primary Examiner — Sharmila G. Landau
Assistant Examiner — Trevor Love
(74) Attorney, Agent, or Firm — Mayer & Williams PC; David B. Bonham; Keum J. Park (57) ABSTRACT The present invention relates generally to medical devices, preferably a stent, having a drug eluting surface coated or covered with a coating of particles comprising at least an outer layer, an inner layer, and a core comprising a therapeutic agent. Specifically, the invention relates to medical devices having a hydrophilic coating comprising particles with a hydrophilic outer layer, a hydrophobic inner layer, and a core comprising a hydrophobic therapeutic agent, as well as medical devices having a hydrophobic coating comprising particles with a hydrophobic outer layer, a hydrophilic inner layer, and a core comprising a hydrophilic therapeutic agent. The coating, outer layer, and inner layer are preferably biodegradable and capable of providing sustained release of the therapeutic agent over a time period. The invention also relates to methods of making and methods of using the coated or covered medical device.

14 Claims, 5 Drawing Sheets

U.S. PATENT DOCUMENTS

| | | | |
|---|---|---|---|
| 2002/0037919 A1 | 3/2002 | Hunter | |
| 2002/0052404 A1 | 5/2002 | Hunter et al. | |
| 2002/0119202 A1 | 8/2002 | Hunter et al. | |
| 2002/0151617 A1 | 10/2002 | Mao et al. | |
| 2002/0155144 A1 | 10/2002 | Troczynski et al. | |
| 2003/0003094 A1 | 1/2003 | Hunter et al. | |
| 2003/0004209 A1 | 1/2003 | Hunter et al. | |
| 2003/0040790 A1* | 2/2003 | Furst | 623/1.11 |
| 2003/0064097 A1 | 4/2003 | Patel et al. | |
| 2003/0099674 A1 | 5/2003 | Chen | |
| 2003/0100600 A1 | 5/2003 | Kinsella et al. | |
| 2003/0125803 A1 | 7/2003 | Vallana et al. | |
| 2003/0129130 A1 | 7/2003 | Guire et al. | |
| 2003/0144570 A1 | 7/2003 | Hunter et al. | |

FOREIGN PATENT DOCUMENTS

| | | | |
|---|---|---|---|
| WO | WO 95/24929 | | 9/1995 |
| WO | WO 98/56312 | * | 12/1998 |
| WO | WO 99/47252 | | 9/1999 |
| WO | WO 00/03797 | | 1/2000 |
| WO | WO 00/13666 | | 3/2000 |
| WO | WO 00/77281 | | 12/2000 |
| WO | WO 01/41821 A1 | | 6/2001 |
| WO | WO 01/51196 | | 7/2001 |
| WO | WO 02/09864 | | 2/2002 |
| WO | WO 02/09865 | | 2/2002 |
| WO | WO 02/17888 | | 3/2002 |
| WO | WO 02/055121 | | 7/2002 |
| WO | WO 02/055122 | | 7/2002 |
| WO | WO 02/085330 A1 | | 10/2002 |
| WO | WO 03/030943 A1 | | 4/2003 |
| WO | WO 2004/000267 A1 | | 12/2003 |
| WO | WO 2005/079754 A2 | | 9/2005 |

OTHER PUBLICATIONS

Antipov et al., 2002, "Polyelectrolyte multilayer capsule permeability control", Colloids and Surfaces A: Physicochem. Eng. Aspects 198-200:535-541.

Donath et al., 1998, "Novel hollow polymer shells: fabrication, characterization and potential applications", Angewandte Chemie 37:2201-2205.

Gopferich, 1996, "Mechanisms of polymer degradation and erosion", Biomaterials 17:103-114.

Moya et al., 2001, "Polyelectrolyte multilayer capsules templated on biological cells: core oxidation influences layer chemistry", Colloids and Surfaces A: Physicochem. Eng. Aspects 183-185:27-40.

Qiu et al., 2001, "Studies on the drug release properties of polysaccharide multilayers encapsulated ibuprofen microparticles", Langmuir 17:5375-5380.

Radtchenko et al., 2000, "Assembly of alternated multivalent ion/polyelectrolyte layers on colloidal particles. Stability of the multilayers and encapsulation of macromolecules into polyelectrolyte capsules", J. Colloid Interface Sci. 230:272-280.

Radtchenko et al., 2002, "A novel method for encapsulation of poorly water-soluble drugs: precipitation in polyelectrolyte multilayer shells", Int. J. Pharm. 242:219-223.

Voight et al., 1999, "Membrane filtration for microencapsulation and microcapsules fabrication by layer-by-layer polyelectrolyte adsorption", Ind. Eng. Chem. Res. 38:4037-4043.

International Search Report of International Application No. PCT/US2005/029529.

* cited by examiner

Fig. 1. Schematic illustration of the changes a polymer matrix undergoes during surface erosion and bulk erosion.

Figure 5

STENTS WITH DRUG ELUTING COATINGS

1. FIELD OF THE INVENTION

The present invention relates generally to medical devices comprising one or more drug eluting coatings. In particular, the invention relates to medical devices, preferably a stent, having a surface coated or covered with a polymeric or non-polymeric material comprising a plurality of particles, preferably nanoparticles, that comprises at least an outer layer, at least an inner layer, and at least a core comprising at least a therapeutic agent, preferably paclitaxel, that inhibits cell proliferation, contraction, migration or hyperactivity or addresses, e.g., prevents or treats other conditions. More particularly, the invention relates to medical devices comprising one or more hydrophilic coatings disposed on a medical device. The coatings comprise particles with one or more hydrophilic outer layers, one or more hydrophobic inner layers, and one or more cores comprising one or more hydrophobic therapeutic agents. Also, the invention relates to medical devices comprising one or more hydrophobic coatings that comprises particles with one or more hydrophobic outer layers, one or more hydrophilic inner layers, and one or more cores comprising one or more hydrophilic therapeutic agents. The coatings as well as the outer layers and inner layers of the particles are preferably biodegradable and capable of providing sustained release of the one or more therapeutic agents over a time period. Methods of manufacturing and methods of using the coated or covered medical device to treat or prevent stenosis or restenosis in a subject, preferably a human, are also provided.

2. BACKGROUND OF THE INVENTION

Cardiovascular disease is a leading cause of death in the developed world. Patients having such disease usually have narrowing or closing (stenosis) in one or more arteries. The use of stents in the treatment of cardiovascular disease is well known. Stents are typically delivered in a contracted state to the treatment area within a lumen, where they are then expanded. Balloon-expandable stents expand from a contracted state by deforming in response to a force exerted upon the stent body by a balloon that is inflated within the stent's lumen. Once expanded within a body lumen, the stent body is strong enough to resist any contracting force exerted by the body lumen wall so that the stent maintains its expanded diameter. In contrast, self-expanding stents have resilient bodies that exert a radial expansion force when the stent is compressed. A self-expanding stent that is deployed within a body lumen will expand until the body lumen wall exerts a compressive force against the stent that is equal to the radial expansion force.

The use of balloon-expandable and self-expanding stents, however, may have the disadvantage of causing additional trauma to a body lumen upon deployment of the stent. Typically, a stent is expanded within a body lumen so that the diameter of the stent is greater than that of the body lumen. As a result, the edges of the ends of stent may be pressed into the wall of body lumen, stressing the wall to the point of creating additional trauma, i.e., cutting or tearing of the body lumen wall. This trauma may ultimately lead to restenosis (re-narrowing) in the areas of the body lumen adjacent the ends of the stent.

Recently, various types of drug-coated stents have been used for the localized delivery of drugs to the wall of a body lumen to further prevent restenosis. However, the hydrophobic or hydrophilic nature of drugs that are used in the coating can impose a number of difficulties on the design of drug delivery coating. For example, with respect to the delivery of a hydrophobic drug like paclitaxel, which is the active ingredient of Taxol®, the hydrophobic drug will tend to cluster inside a hydrophilic coating and as a result, will not be evenly distributed throughout the coating. On the other hand, when using a hydrophobic matrix that allows an even distribution of the hydrophobic drug, it is difficult to get a 100% release of the hydrophobic drug into a hydrophilic environment as the hydrophobic drug will be more inclined to remain inside the hydrophobic matrix environment.

Similarly, when using a block-polymer with both hydrophobic and hydrophilic side-branches, one will get a self-assembly of the alike structures whereby the hydrophobic drug will be attached to the regions of the highest hydrophobicity and therefore, making it difficult to release the hydrophobic drug in an effective and consistent manner. Similarly, a hydrophilic drug will be attached to the region of highest hydrophilicity, thereby making effective and consistent release of the drug difficult.

The use of biodegradable coatings has also been proposed as a possible solution to release the hydrophobic drug into a hydrophilic environment because of the erosion or degradation of the surrounding matrix. However, as in the case of using a hydrophobic matrix, it is difficult to obtain a steady and complete release of the hydrophobic drug because the hydrophobic drug will be more inclined to stay in the remaining hydrophobic coating even as the hydrophobic coating degrades. The delivery of a hydrophilic drug to an environment that is hydrophobic or less hydrophilic relative to the hydrophilic drug may be equally challenging.

In order to optimize drug delivery, one has to solve the contradiction of a hydrophobic drug that needs to act as hydrophilic or vice versa.

3. SUMMARY OF THE INVENTION

To achieve the aforementioned objectives, the inventor has invented insertable or implantable medical devices comprising hydrophilic or hydrophobic drug eluting coatings. Methods of making and using the medical device are also provided.

The invention relates to medical devices comprising a surface and a coating disposed on the surface. In specific embodiments, the invention relates to medical devices comprising one or more hydrophilic or hydrophobic coatings that comprise particles comprising one or more outer layers, one or more inner layers, and one or more cores. In a specific embodiment, a coating comprises a first hydrophilic polymeric or non-polymeric material incorporating a plurality of particles comprising an outer layer, an inner layer, and a core comprising a therapeutic agent. In another specific embodiment, a coating comprises a first hydrophobic polymeric or non-polymeric material incorporating a plurality of particles comprising an outer layer, an inner layer, and a core comprising a therapeutic agent. The outer and inner layers of the particles comprise either a hydrophilic or a hydrophobic polymeric or non-polymeric material. In specific embodiments, the therapeutic agent is hydrophobic or hydrophilic.

In certain embodiments, the medical device comprises at least one coating comprising a first hydrophilic polymeric material incorporating a plurality of particles comprising an outer layer comprising a second hydrophilic polymeric material, an inner layer comprising a first hydrophobic polymeric material, and a core comprising a hydrophobic therapeutic agent. In a specific embodiment, the first and second hydrophilic polymeric materials are the same. In another specific embodiment, the first and/or second hydrophilic polymeric materials are biodegradable. In yet another specific embodiment, the hydrophilic polymeric material comprises polyvinyl alcohol (PVA) and/or poly(L-lactide) (PLLA).

In certain other embodiments, the medical device comprises at least one coating comprising a first hydrophobic polymeric material incorporating a plurality of particles comprising an outer layer comprising a second hydrophobic polymeric material, an inner layer comprising a first hydrophilic polymeric material, and a core comprising a hydrophilic therapeutic agent. In a specific embodiment, the first and second hydrophobic polymeric materials are the same. In another specific embodiment, the first and/or second hydrophobic polymeric materials are biodegradable. In yet another specific embodiment, the hydrophobic polymeric material comprises copolymers of styrene and isobutylene, polyorthoesters and/or polyanhydrides.

In certain embodiments, the medical device comprises at least one coating comprising a first hydrophilic non-polymeric material incorporating a plurality of particles comprising an outer layer comprising a second hydrophilic non-polymeric material, an inner layer comprising a first hydrophobic non-polymeric material, and a core comprising a hydrophobic therapeutic agent. In a specific embodiment, the first and second hydrophilic non-polymeric materials are the same. In another specific embodiment, the first and/or second hydrophilic non-polymeric materials are biodegradable. In yet another specific embodiment, the hydrophilic non-polymeric material comprises myristyl alcohol. In yet another specific embodiment, the hydrophilic non-polymeric material comprises carbon structures such as carbon tubes or balls, which can be made hydrophilic by attaching carboxylic acid groups by means of an acid treatment.

In certain other embodiments, the medical device comprises at least one coating comprising a first hydrophobic non-polymeric material incorporating a plurality of particles comprising an outer layer comprising a second hydrophobic non-polymeric material, an inner layer comprising a first hydrophilic non-polymeric material, and a core comprising a hydrophilic therapeutic agent. In a specific embodiment, the first and second hydrophobic non-polymeric materials are the same. In another specific embodiment, the first and/or second hydrophobic non-polymeric materials are biodegradable. In yet another specific embodiment, the hydrophobic non-polymeric material comprises cholesterol. In yet another specific embodiment, the hydrophobic non-polymeric material comprises liposomes.

In a specific embodiment, the particles comprises nanoparticles, preferably particles of size ranging from 1 to 100 nanometer (nm) in diameter. In another specific embodiment, the particles comprises capsules, preferably nano-sized capsules, or capsules of size ranging from 1 to 100 nm in diameter.

In certain embodiments, the particles comprise one or more outer layers, one or more inner layers, and one or more cores. In one embodiment, the particles comprise one, two, three, four, five or more outer layers. In one embodiment, the particles comprise one, two, three, four, five or more inner layers. In one embodiment, the particles comprise one, two, three, four, five or more cores. In a specific embodiment, the particles comprise one outer layer, one inner layer, and one core. In one embodiment, one or more inner layers of the particles are biodegradable. In another embodiment, one or more outer layers of the particles are biodegradable.

In certain embodiments, the particles comprise at least an outer layer comprising one or more hydrophilic polymeric or non-polymeric materials, at least an inner layer comprising one or more hydrophobic polymeric or non-polymeric materials, and at least a core. In certain embodiments, the particles comprise at least an outer layer comprising one or more hydrophobic polymeric or non-polymeric materials, at least an inner layer comprising one or more hydrophilic polymeric or non-polymeric materials, and at least a core. In a specific embodiment, the hydrophilic and hydrophobic polymeric or non-polymeric materials are biodegradable.

In a specific embodiment, the core comprises a hydrophobic therapeutic agent, preferably paclitaxel. In another specific embodiment, the core comprises a hydrophilic therapeutic agent, preferably heparin or urikinase.

In certain embodiments, the medical device comprises one or more coatings. The one or more coatings may be layered on top of each other or disposed on different parts of a surface of the medical device. In a specific embodiment, the medical device comprises one coating. In another specific embodiment, the surface comprises a ceramic layer.

In a specific embodiment, the coating is biodegradable. In a specific embodiment, the coating is hydrophilic. In a preferred embodiment, the hydrophilic coating comprises polyvinyl alcohol (PVA) or poly(L-lactide) (PLLA). In another specific embodiment, the coating is hydrophobic. In a preferred embodiment, the hydrophobic coating comprises copolymers of styrene and isobutylene, polyorthoesters and/or polyanhydrides.

In one embodiment, the coating comprises a plurality of particles comprising one or more therapeutic agents. In a preferred embodiment, the particles are evenly dispersed in the coating.

In certain embodiments, the coating comprises a therapeutically effective amount of one or more therapeutic agents. In a specific embodiment, the coating comprises a therapeutically effective amount of one therapeutic agent. In a specific embodiment, the one or more therapeutic agents inhibit cell proliferation, contraction, migration or hyperactivity. In a preferred embodiment, the cell is a muscle cell, preferably a smooth muscle cell. In other embodiments, the one or more therapeutic agents, e.g., anti-inflammatory drugs, prevent or treat other conditions such as inflammation surrounding vulnerable plaque. In other embodiments, prevent or treat other conditions such as cancer.

In certain embodiments, the coating is capable of providing sustained release of one or more therapeutic agents over a time period. The time period for release of a therapeutic agent from the coating ranges from 1 hour, 2 hours, 3 hours, 4 hours, 5 hours, 6 hours, 12 hours, 1 day, 2 days, 3 days, 4 days, 5 days, 6 days, 1 week, 2 weeks, 3 weeks, 1 month, 2 months, 3 months, 4 months, 5 months, 6 months, 1 year, 2 years, or longer. Preferably, the time period for release of the therapeutic agent from the coating ranges from 1 hour to 24 months.

The particles and coating comprising the particles can be directly or locally administered into a subject to inhibit cell proliferation, contraction, migration, hyperactivity, or address other conditions. In a specific embodiment, cell proliferation, contraction, migration or hyperactivity is inhibited locally, e.g., at the site of administration. In another specific embodiment, cell proliferation, contraction, migration or hyperactivity is inhibited systemically, e.g., at a site that is different from the site of administration. Methods of administering the particles and coatings of the invention include, but are not limited to, parenteral (e.g., subcutaneous, intramuscular, intraorbital, intracapsular, intraspinal, intrasternal, intravenous, intradermal, intraperitoneal, intraportal), epidural, and mucosal (e.g., intranasal) injection or infusion. The particles and coatings can also be implanted into a subject. In a specific embodiment, a magnetic kernel can be introduced into the particle and the particles, once implanted into the subject, can be directed by external magnetic fields.

The invention also relates to medical devices, preferably stents, comprising one or more therapeutic agents. In one embodiment, a medical device comprises particles that comprises one or more outer layers, one or more inner layers, and one or more cores comprising a therapeutic agent. In another embodiment, a medical device comprises a coating comprising particles that comprises one or more outer layers, one or more inner layers, and one or more cores comprising a therapeutic agent.

The medical device is suitable for insertion or implantation into a subject, preferably a human. Preferably, the medical device is a stent.

The invention also relates to methods for treating or preventing stenosis or restenosis or addressing other conditions comprising inserting or implanting the medical device into a subject in need thereof. The medical device may be inserted or implanted alone or in combination with other treatment protocols.

3.1 Definitions

As used herein, the term "hydrophilic" refers to the characteristics of readily absorbing or dissolving in water, having polar groups (in which the distribution of electrons is uneven, enabling it to take part in electrostatic interactions) that readily interact with water, and/or having an affinity for water.

As used herein, the term "hydrophobic" refers to the characteristics of not readily absorbing or dissolving in water, being adversely affected by water, and/or having little or no affinity for water.

As used herein, the term "amphiphilic" refers to the characteristics of having both hydrophilic and hydrophobic properties.

As used herein, the term "therapeutically effective amount" refers to that amount of the therapeutic agent sufficient to inhibit cell-proliferation, contraction, migration, hyperactivity, or address other conditions. A therapeutically effective amount may refer to the amount of therapeutic agent sufficient to delay or minimize the onset of symptoms associated with cell proliferation, contraction, migration, hyperactivity, or address other conditions. A therapeutically effective amount may also refer to the amount of the therapeutic agent that provides a therapeutic benefit in the treatment or management of certain conditions such as stenosis or restenosis and/or the symptoms associated with stenosis or restenosis.

As used herein, the terms "subject" and "patient" are used interchangeably. As used herein, a subject is preferably a mammal such as a non-primate (e.g., cows, pigs, horses, cats, dogs, rats, etc.) and a primate (e.g., monkey and human), most preferably a human.

As used herein, the prefix "nano-" means $10^{-9}$.

4. FIGURES

FIG. 1 shows a first preferred embodiment of a medical device of the present invention. The medical device comprises a surface (1a) and a coating (1b) disposed on the surface (1a). The coating (1b) comprises a first hydrophilic polymeric material (1c) incorporating a plurality of particles (1d). Each particle (1d) comprise an outer layer (1e) comprising a second hydrophilic polymeric material, an inner layer (1f) comprising a hydrophobic polymeric material, and a core (1g) comprising a hydrophobic therapeutic agent.

FIG. 2 shows a second preferred embodiment of a medical device of the present invention. The medical device comprises a surface (2a) and a coating (2b) disposed on the surface (2a). The coating (2b) comprises a first hydrophobic polymeric material (2c) incorporating a plurality of particles (2d). Each particle (2d) comprise an outer layer (2e) comprising a second hydrophobic polymeric material, an inner layer (2f) comprising a hydrophilic polymeric material, and a core (2g) comprising a hydrophilic therapeutic agent.

FIG. 5 shows a schematic illustration of the changes a polymer matrix undergoes during surface erosion and bulk erosion.

5. DETAILED DESCRIPTION OF THE INVENTION

The present invention relates to medical devices comprising one or more coatings that elute therapeutic agents. Specifically, the one or more such eluting coatings comprise at least one polymeric materials incorporating a plurality of particles such that each particle comprises at least an outer layer, at least an inner layer, and at least a core containing a therapeutic agent. In a specific embodiment, a coating comprises a first polymeric material comprising particles that comprise an outer layer comprising a second polymeric material, an inner layer comprising a third polymeric material, and a core comprising a therapeutic agent. The first, second, and third polymeric materials can be either hydrophilic or hydrophobic. The therapeutic agent can be either hydrophilic or hydrophobic. In a specific embodiment, the third polymeric material and therapeutic agent are hydrophilic. In a specific embodiment, the third polymeric material and therapeutic agent are hydrophobic. In a specific embodiment, the first and second polymeric materials are the same.

Figure 1:
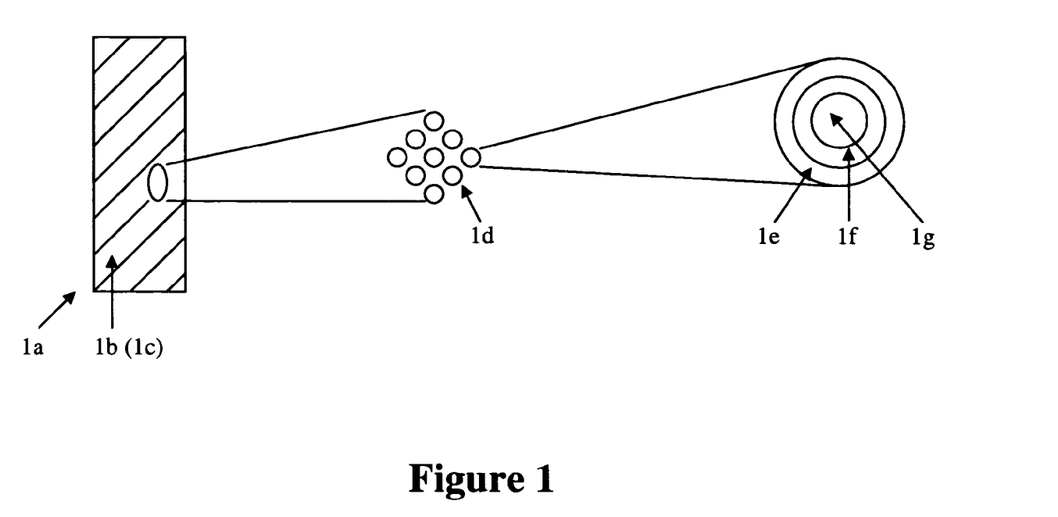
Figure 2:
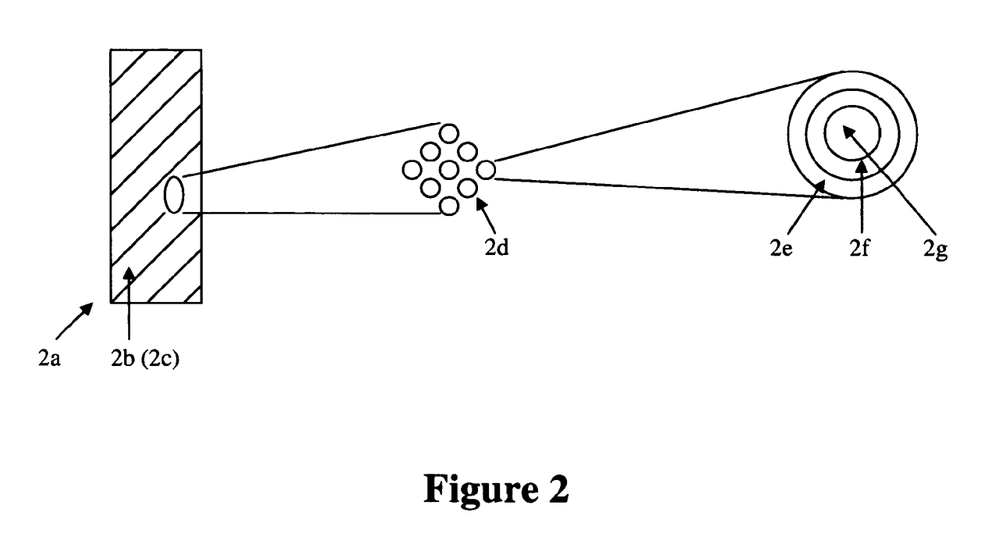

In a preferred embodiment, a coating comprises a first hydrophilic polymeric material incorporating a plurality of particles that comprise an outer layer comprising a second hydrophilic polymeric material, an inner layer comprising a first hydrophobic polymeric material, and a core comprising a hydrophobic therapeutic agent (see FIG. 1). In another preferred embodiment, a coating comprises a first hydrophobic polymeric material incorporating a plurality of particles that comprise an outer layer comprising a second hydrophobic polymeric material, an inner layer comprising a first hydrophilic polymeric material, and a core comprising a hydrophilic therapeutic agent (see FIG. 2). Hydrophobic coatings generally have much longer degradation times than hydrophilic coatings due to the fact that water cannot penetrate into them as easily. Depending on the application, one may want to have a quickly dissolving coating (hydrophilic) releasing a hydrophobic drug, or a slowly dissolving coating (hydrophobic) releasing a hydrophilic drug. One objective of the present invention is to allow a uniform delivery of the drug as the drug is driven out of the coating as soon as the particles that make up the coating is dissolved.

Although not to be limited in theory, the combination of a hydrophilic or hydrophobic drug eluting coating and particles with alternating and/or multiple hydrophilic and hydrophobic layers provides a microenvironment that allow the efficient and consistent release of one or more therapeutic agents to inhibit cell proliferation, contraction, migration, hyperactivity or other conditions.

For clarity of disclosure, and not by way of limitation, the detailed description of the invention is divided into the subsections which follow.

5.1 Methods for Making the Medical Devices 5.1.1 Methods for Preparing the Particles The particles used in the medical device of the invention comprises one or more outer layers, one or more inner layers, and one or more cores comprising one or more therapeutic agents. In a specific embodiment, a particle comprises an outer layer, an inner layer, and a core comprising a therapeutic agent.

In a preferred embodiment, the particle is a nanoparticle, i.e., a nano-sized particle. In another preferred embodiment, the particle is a capsule. More preferably, the capsule is a nano-sized capsule. In specific embodiments, the particle is 1 μm, 5 μm, 10 μm, 50 μm, 100 μm, 1 nm, 5 nm, 10 nm, 20 nm, 30 nm, 40 nm, 50 nm, 60 nm, 70 nm, 80 nm, 90 nm, 100 nm, 500 nm, or 1,000 nm in diameter.

In one embodiment, the outer layer of the particle comprises a first polymeric material and the inner layer of the particle comprises a second polymeric material. In a specific embodiment, the first and second polymeric materials are different. In a specific embodiment, the first and second polymeric materials have opposing hydrophobicity or hydrophilicity. In another specific embodiment, the first and second polymeric materials are amphiphilic.

In a preferred embodiment, the first polymeric material is hydrophilic and the second polymeric material is hydrophobic. In another preferred embodiment, the first polymeric material is hydrophobic and the second polymeric material is hydrophilic. In a less preferred embodiment, the first and second polymeric materials are both hydrophilic or hydrophobic.

In preferred embodiments, the first and second polymeric materials are biodegradable.

Suitable polymeric materials for forming particles are further described in Section 5.1.3 infra. Examples of preferred polymeric materials for forming particles include, but are not limited to, PVA, PLLA, copolymers of styrene and isobutylene, polyorthoesters, and polyanhydrides.

In specific embodiments, the particle comprises one or more cores comprising a therapeutic agent.

In certain embodiments, the therapeutic agent is useful for inhibiting cell proliferation, contraction, migration, hyperactivity, or addressing other conditions. The term "therapeutic agent" encompasses drugs, genetic materials, and biological materials. Non-limiting examples of suitable therapeutic agent include heparin, heparin derivatives, urokinase, dextrophenylalanine proline arginine chloromethylketone (PPack), enoxaprin, angiopeptin, hirudin, acetylsalicylic acid, tacrolimus, everolimus, rapamycin (sirolimus), amlodipine, doxazosin, glucocorticoids, betamethasone, dexamethasone, prednisolone, corticosterone, budesonide, sulfasalazine, rosiglitazone, mycophenolic acid, mesalamine, paclitaxel, 5-fluorouracil, cisplatin, vinblastine, vincristine, epothilones, methotrexate, azathioprine, adriamycin, mutamycin, endostatin, angiostatin, thymidine kinase inhibitors, cladribine, lidocaine, bupivacaine, ropivacaine, D-Phe-Pro-Arg chloromethyl ketone, platelet receptor antagonists, anti thrombin antibodies, anti platelet receptor antibodies, aspirin, dipyridamole, protamine, hirudin, prostaglandin inhibitors, platelet inhibitors, trapidil, liprostin, tick antiplatelet peptides, 5-azacytidine, vascular endothelial growth factors, growth factor receptors, transcriptional activators, translational promoters, antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, cholesterol lowering agents, vasodilating agents, agents which interfere with endogenous vasoactive mechanisms, antioxidants, probucol, antibiotic agents, penicillin, cefoxitin, oxacillin, tobranycin, angiogenic substances, fibroblast growth factors, estrogen, estradiol (E2), estriol (E3), 17-beta estradiol, digoxin, beta blockers, captopril, enalopril, statins, steroids, vitamins, taxol, paclitaxel, 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, 2'-O-ester with N-(dimethylaminoethyl) glutamide hydrochloride salt, nitroglycerin, nitrous oxides, nitric oxides, antibiotics, aspirins, digitalis, estrogen, estradiol and glycosides. In a preferred embodiment, the therapeutic agent is taxol (e.g., Taxol®), or its analogs or derivatives. In another preferred embodiment, the therapeutic agent is paclitaxel. In yet another preferred embodiment, the therapeutic agent is an antibiotic such as erythromycin, amphotericin, rapamycin, adriamycin, etc.

The term "genetic materials" means DNA or RNA, including, without limitation, of DNA/RNA encoding a useful protein stated below, intended to be inserted into a human body including viral vectors and non-viral vectors.

The term "biological materials" include cells, yeasts, bacteria, proteins, peptides, cytokines and hormones. Examples for peptides and proteins include vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factors (CGF), platelet-derived growth factor (PDGF), hypoxia inducible factor-1 (HIF-1), stem cell derived factor (SDF), stem cell factor (SCF), endothelial cell growth supplement (ECGS), granulocyte macrophage colony stimulating factor (GM-CSF), growth differentiation factor (GDF), integrin modulating factor (IMF), calmodulin (CaM), thymidine kinase (TK), tumor necrosis factor (TNF), growth hormone (GH), bone morphogenic protein (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, etc.), matrix metalloproteinase (MMP), tissue inhibitor of matrix metalloproteinase (TIMP), cytokines, interleukin (e.g., IL-1, IL-2, IL-3, IL-4, IL-5, IL-6, IL-7, IL-8, IL-9, IL-10, IL-11, IL-12, IL-15, etc.), lymphokines, interferon, integrin, collagen (all types), elastin, fibrillins, fibronectin, vitronectin, laminin, glycosaminoglycans, proteoglycans, transferrin, cytotactin, cell binding domains (e.g., RGD), and tenascin. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include progenitor cells (e.g., endothelial progenitor cells), stem cells (e.g., mesenchymal, hematopoietic, neuronal), stromal cells, parenchymal cells, undifferentiated cells, fibroblasts, macrophage, and satellite cells.

Other non-genetic therapeutic agents include:

anti-thrombogenic agents such as heparin, heparin derivatives, urokinase, and PPack (dextrophenylalanine proline arginine chloromethylketone);

anti-proliferative agents such as enoxaprin, angiopeptin, or monoclonal antibodies capable of blocking smooth muscle cell proliferation, hirudin, acetylsalicylic acid, tacrolimus, everolimus, amlodipine and doxazosin;

anti-inflammatory agents such as glucocorticoids, betamethasone, dexamethasone, prednisolone, corticosterone, budesonide, estrogen, sulfasalazine, rosiglitazone, mycophenolic acid and mesalamine;

anti-neoplastic/anti-proliferative/anti-miotic agents such as paclitaxel, 5-fluorouracil, cisplatin, vinblastine, vincristine, epothilones, methotrexate, azathioprine, adriamycin, mutamycin, endostatin, angiostatin, thymidine kinase inhibitors, cladribine, taxol and its analogs or derivatives;

anesthetic agents such as lidocaine, bupivacaine, and ropivacaine;

anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors, antiplatelet agents such as trapidil or liprostin and tick antiplatelet peptides;

DNA demethylating drugs such as 5-azacytidine, which is also categorized as a RNA or DNA metabolite that inhibit cell growth and induce apoptosis in certain cancer cells;

vascular cell growth promoters such as growth factors, vascular endothelial growth factors (VEGF, all types including VEGF-2), growth factor receptors, transcriptional activators, and translational promoters;

vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents; vasodilating agents; and agents which interfere with endogenous vasoactive mechanisms;

anti-oxidants, such as probucol;

antibiotic agents, such as penicillin, cefoxitin, oxacillin, tobranycin, macrolides such as rapamycin (sirolimus) and everolimuns;

angiogenic substances, such as acidic and basic fibroblast growth factors, estrogen including estradiol (E2), estriol (E3) and 17-beta estradiol; and drugs for heart failure, such as digoxin, beta-blockers, angiotensin-converting enzyme (ACE) inhibitors including captopril and enalopril, statins and related compounds. Preferred biologically active materials include anti-proliferative drugs such as steroids, vitamins, and restenosis-inhibiting agents. Preferred restenosis-inhibiting agents include microtubule stabilizing agents such as Taxol®, paclitaxel (i.e., paclitaxel, paclitaxel analogues, or paclitaxel derivatives, and mixtures thereof). For example, derivatives suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

Other preferred therapeutic agents include nitroglycerin, nitrous oxides, nitric oxides, antibiotics, aspirins, digitalis, estrogen derivatives such as estradiol and glycosides.

In certain embodiments, the therapeutic agents for use in the medical devices of the present invention can be synthesized by methods well known to one skilled in the art. Alternatively, the therapeutic agents can be purchased from chemical and pharmaceutical companies.

In one embodiment, one or more therapeutic agents are encapsulated into a particle. In a preferred embodiment, a particle comprises one therapeutic agent.

The therapeutic agents can be incorporated into the particle of the present invention by methods well known to one skilled in the art (see, e.g., Radtchenko et al., A novel method for encapsulation of poorly water-soluble drugs: precipitation in polyelectrolyte multilayer shells. *Int J. Pharm.* 2002; 242: 219-23; Antipov et al. Polyelectrolyte multilayer capsule permeability control. *Colloids and Surfaces A: Physiocochem Eng Aspects* 2002; 198-200: 535-541; Qiu et al. Studies on the drug release properties of polysaccharide multilayers encapsulated ibuprofen microparticles. *Langmuir* 2001; 17: 5375-5380; Moya et al. Polyelectrolyte multilayer capsules templated on biological cells: core oxidation influences layer chemistry. *Colloids and Surfaces A: Physiocochem Eng Aspects* 2001; 183-185: 27-40; Radtchenko et al. Assembly of Alternated Multivalent Ion/Polyelectrolyte Layers on Colloidal Particles. Stability of the Multilayers and Encapsulation of Macromolecules into Polyelectrolyte Capsules. *J Colloid Interface Sci.* 2000; 230: 272-280; Voigt et al. Membrane filtration for microencapsulation and microcapsules fabrication by layer-by-layer polyelectrolyte adsorption. *Ind Eng Chem Res.* 1999; 38: 4037-4043; Donath et al. Novel hollow polymer shells: fabrication, characterization and potential applications. *Angewandte Chemie* 1998; 37: 2201-2205; International Publication No. WO 95/08320; and U.S. Pat. No. 6,322,817 issued to Maitra et al. and U.S. Pat. No. 6,007,845 issued to Domb et al., each of which is incorporated by reference herein in its entirety).

Figure 3:
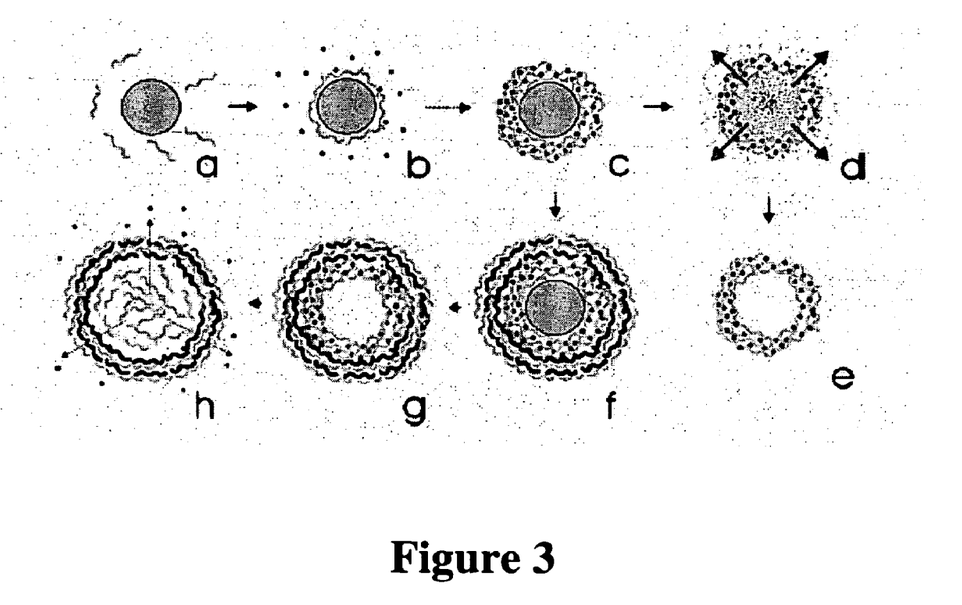
FIG. 3 shows layer-by-layer assembly of multicharged ions (dots) and polyelectrolytes (curves) on colloidal particles (a, b, c), decomposition of colloidal core (d), formation of hollow capsules composed of multicharged ion/polyelectrolyte complexes (e), or sequential assembly of a stable polyelectrolyte shell (f), and then core decomposition with double-shell formation capsules (g) and dissolution of polyelectrolyte from the degradable inner part of the shell to the interior (h). See Radtchenko et al., A novel method for encapsulation of poorly water-soluble drugs: precipitation in polyelectrolyte multilayer shells. *Int J. Pharm.* 2002; 242: 219-23, which is incorporated by reference herein in its entirety.

In a specific embodiment, a therapeutic agent is directly encapsulated into a particle. In another specific embodiment, a therapeutic agent is precipitated into hollow capsules. In another specific embodiment, a therapeutic agent is encapsulated into a particle using inverse microemulsion. In another specific embodiment, a therapeutic agent is incorporated into a particle using layer-by-layer techniques (see Radtchenko et al. supra.; FIG. 3).

In one embodiment, paclitaxel is encapsulated into nanoparticles of co-polymeric micelles comprising the steps of: (a) dissolving at least one type of amphiphilic monomer selected from the group consisting of vinylpyrrolidone, acrylic acid, alkyl acrylates having a chain length of $C_3$ to $C_6$ functionalized polyethylene glycol of a molecular weight of 2000 to 6000, N-alkylacrylamide having a chain length of $C_3$ to $C_6$, and alkylcyanoacrylate having a chain length of $C_3$ to $C_6$, in an aqueous medium to obtain micelles; (b) polymerizing the micelles by adding an aqueous solution of cross-linking agent; (c) polymerizing the solution in the presence of an inert gas at 20° C. to 80° C. until the polymerization of micelles is complete; (d) dialysing the solution of nanoparticles of polymerized micelles to remove toxic monomer and other unreacted materials; and (e) adding an alcoholic solution of paclitaxel, i.e., paclitaxel, its derivatives or analogs, to the nanoparticles of polymerized micelles.

In another embodiment, the therapeutic agents are encapsulated into nanoparticles using LBL-technology® (Capsulution NanoScience AG, Berlin, Germany) as described in International Publication Nos. WO 99/47252, WO 00/03797, WO 00/77281, WO 02/09864; WO 01/51196), WO 02/09865 and WO 02/17888. In a specific embodiment, therapeutic agents are encapsulated into nanoparticles in a layer-by-layer fashion. First, a nano-scaled particle is generated by colloid mills, jet mills or precipitation techniques. Second, the nanocapsule is suspended in an aqueous phase. Third, a charge (e.g., a positive (+) charge) is induced on the surface of the nanocapsule. Fourth, an oppositely charged polyelectrolyte (e.g., an anionic (−) specie) is added to form a first layer on the surface of the nanocapsule. Fifth, an oppositely charged polyelectrolyte (e.g., a cationic (+) specie) is added to form a second layer on the surface of the nanocapsule. A nanocapsule with two or more polyelectrolytes forms a stable complex. In one embodiment, the particles used in the present invention comprises one, two, three, four, five or more layers. Non-limiting examples of polyelectrolytes include (1) cationic species (e.g., protamine sulfate, polyallylamine, polydiallyldimethylammoniume, polyethleneimine, chitosan, eudragit, gelatine, spermidine, albumin, etc.) and (2) anionic species (e.g., polyacrylic acid, sodium alginate, polystyrene sulfonate, eudragit, gelatine, hyaluronic acid, carrageenan, chondroitin sulfate, carboxymethylcellulose, etc.). The LBL-technology® can be used to prepare particles having a hydrophilic outer layer and a hydrophobic inner layer as well as particles having a hydrophobic outer layer and a hydrophilic inner later.

In certain embodiments, the particles can be labeled with, e.g., radioisotopes, antibodies, or colored with, e.g., dye.

5.1.2 Methods for Preparing the Drug Eluting Coating

Coating compositions suitable for forming coatings to the devices of the present invention can include a polymeric material as described in Section 5.1.3 infra. and the particles as described in Section 5.1.1 supra. In one embodiment, the coating comprises a plurality of particles comprising at least an outer layer, at least an inner layer, and at least a core comprising a therapeutic agent. In one embodiment, the coating comprises a plurality of particles comprising an outer layer, an inner layer, and a core comprising a therapeutic agent Optionally, the coating composition can further comprise a therapeutic agent, such as those described in Section 5.1.1 supra. A coating composition comprising such additional therapeutic agent would result in a coating comprising the polymer, particles and the additional therapeutic agent. In one embodiment, the coating comprises a plurality of particles comprising the same therapeutic agent. In another specific embodiment, the plurality of particles comprises particles that comprises different therapeutic agents.

To prepare the coating compositions, the constituents, i.e., polymer, particles and optionally an additional therapeutic agent, are suspended and/or dissolved in a solvent. Preferably, the solvent does not alter or adversely impact the therapeutic properties of the therapeutic agents employed. For example, useful solvents for silicone include tetrahydrofuran (THF), chloroform, toluene, acetone, isooctane, 1,1,1-trichloroethane, dichloromethane, and mixture thereof.

In specific embodiments, the coating compositions comprises at least 5%, at least 10%, at least 20%, at least 30%, at least 40%, at least 50%, at least 60%, at least 70%, at least 80%, at least 90%, at least 97%, at least 99% or more by weight of the polymer. In specific embodiments, the coating compositions comprises at least 5%, at least 10%, at least 20%, at least 30%, at least 40%, at least 50%, at least 60%, at least 70%, at least 80%, at least 90%, at least 95%, at least 97%, at least 99% or more by weight of the particles. In specific embodiments, the coating compositions comprises at least 5%, at least 10%, at least 20%, at least 30%, at least 40%, at least 50%, at least 60%, at least 70%, at least 80%, at least 90%, at least 95%, at least 97%, at least 99% or more by weight of the additional therapeutic agent.

5.1.3 Polymeric Materials

The polymeric material suitable for use in the preparation of the particles and the drug eluting coatings of the present invention should be a material that is biocompatible and avoids irritation to body tissue. Preferably, the polymeric materials used in the particles and coating compositions of the present invention are selected from the following: polyurethanes, silicones (e.g., polysiloxanes and substituted polysiloxanes), and polyesters. Also preferable as a polymeric material is copolymers of styrene and isobutylene, or more preferably, styrene-isobutylene-styrene (SIBS). Other polymers which can be used include ones that can be dissolved and cured or polymerized on the medical device or polymers having relatively low melting points that can be blended with biologically active materials. Additional suitable polymers include, thermoplastic elastomers in general, polyolefins, polyisobutylene, ethylene-alphaolefin copolymers, acrylic polymers and copolymers, vinyl halide polymers and copolymers such as poly(lactide-co-glycolide) (PLGA), polyvinyl alcohol (PVA), poly(L-lactide) (PLLA), polyanhydrides, polyphosphazenes, polycaprolactone (PCL), polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate, copolymers of vinyl monomers, copolymers of vinyl monomers and olefins such as ethylene-methyl methacrylate copolymers, acrylonitrile-styrene copolymers, ABS (acrylonitrile-butadiene-styrene) resins, ethylene-vinyl acetate copolymers, polyamides such as Nylon 66 and polycaprolactone, alkyd resins, polycarbonates, polyoxymethylenes, polyimides, polyethers, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid (PLA), polyglycolic acid (PGA), polyethylene oxide (PEO), polylactic acid-polyethylene oxide copolymers, EPDM (etylene-propylenediene) rubbers, fluorosilicones, polyethylene glycol (PEG), polyalkylene glycol (PAG), polysaccharides, phospholipids, and combinations of the foregoing.

In certain embodiments, the polymeric material is hydrophilic (e.g., PVA, PLLA, PLGA, PEG, and PAG). In certain other embodiments, the polymeric material is hydrophobic (e.g., PLA, PGA, polyanhydrides, polyphosphazenes, PCL, copolymers of styrene and isobutylene, and polyorthoesters).

More preferably for medical devices which undergo mechanical challenges, e.g. expansion and contraction, the polymeric materials should be selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. Because of the elastic nature of these polymers, the coating composition is capable of undergoing deformation under the yield point when the device is subjected to forces, stress or mechanical challenge.

In preferred embodiments, the polymeric materials are biodegradable. Biodegradable polymeric materials can degrade as a result of hydrolysis of the polymer chains into biologically acceptable, and progressively smaller compounds. In one embodiment, a polymeric material comprises polylactides, polyglycolides, or their co-polymers. Polylactides, polyglycolides, and their co-polymers break down to lactic acid and glycolic acid, which enters the Kreb's cycle and are further broken down into carbon dioxide and water.

Figures 1, 5:
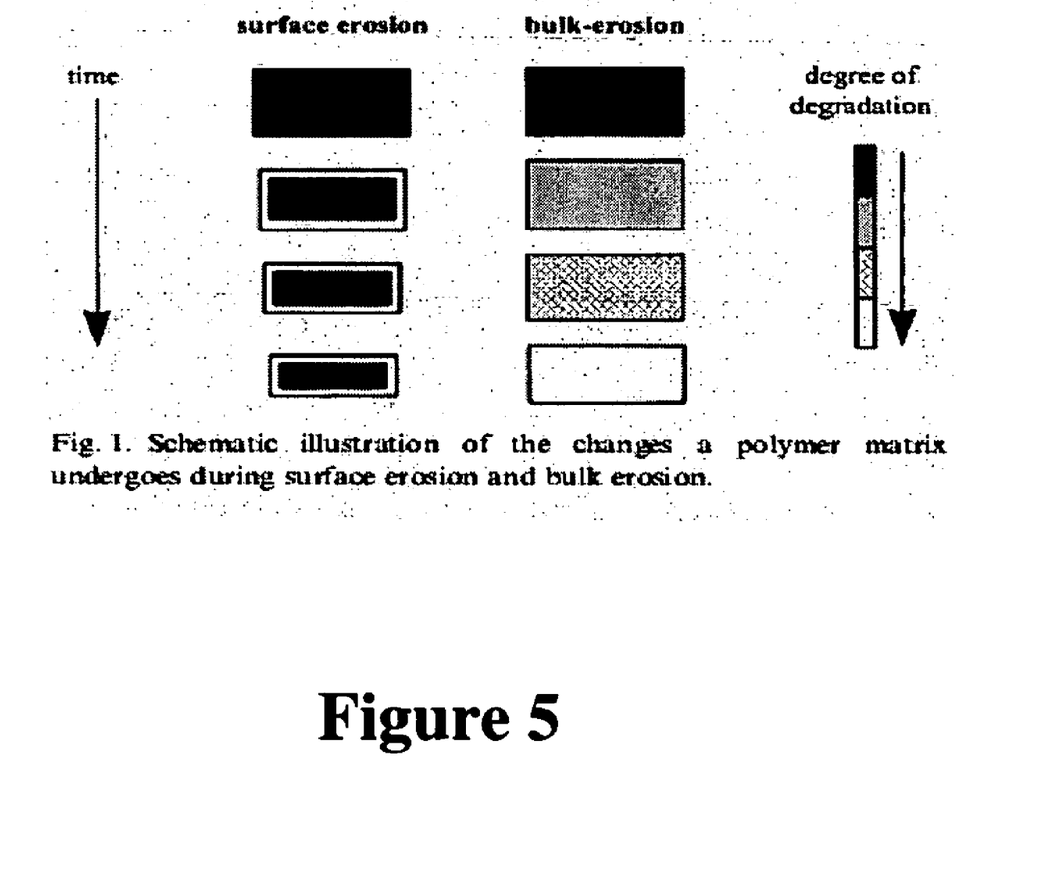
Figure 4:
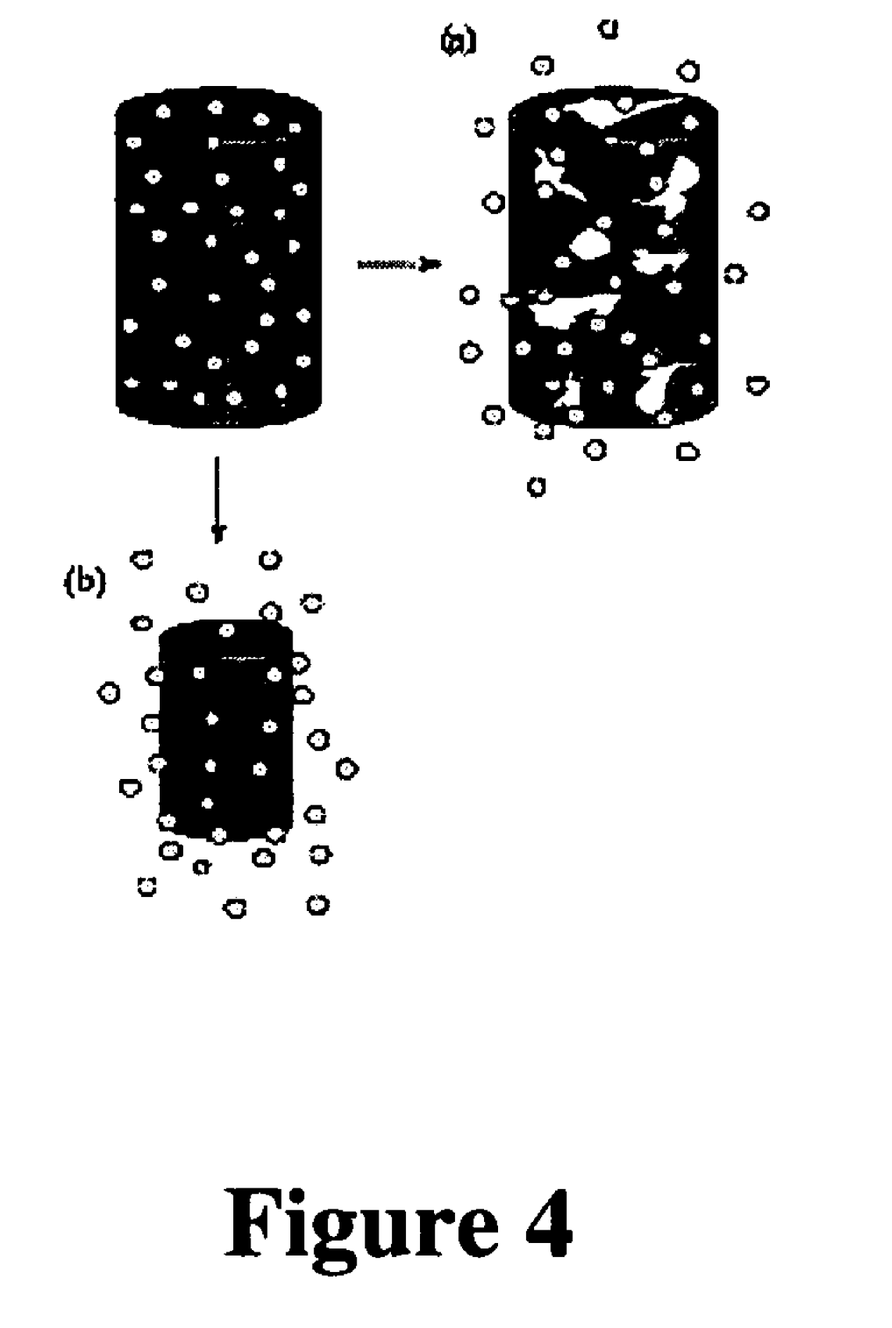
FIG. 4 shows drug delivery from biodegradable coatings by bulk hydrolysis.

Biodegradable solids may have differing modes of degradation. On one hand, degradation by bulk erosion/hydrolysis occurs when water penetrates the entire structure and degrades the entire structure simultaneously, i.e., the polymer degrades in a fairly uniform manner throughout the structure (see FIG. 4). On the other hand, degradation by surface erosion occurs when degradation begins from the exterior with little/no water penetration into the bulk of the structure (see FIG. 5) (see Gopferich A. Mechanisms of polymer degradation and erosion. *Biomaterials* 1996; 17(103):243-259, which is incorporated by reference herein in its entirety). For some novel degradable polymers, most notably the polyanhydrides and polyorthoesters, the degradation occurs only at the surface of the polymer, resulting in a release rate that is proportional to the surface area of the drug delivery system. Hydrophilic polymeric materials such as PLGA will erode in a bulk fashion. Various commercially available PLGA may be used in the preparation of the coating compositions. For example, poly(d,l-lactic-co-glycolic acid) are commercially available. A preferred commercially available product is a 50:50 poly (D,L) lactic co-glycolic acid having a mole percent composition of 50% lactide and 50% glycolide. Other suitable commercially available products are 65:35 DL, 75:25 DL, 85:15 DL and poly(d,l-lactic acid) (d,l-PLA). For example, poly(lactide-co-glycolides) are also commercially available from Boehringer Ingelheim (Germany) under its Resomer©, e.g., PLGA 50:50 (Resomer RG 502), PLGA 75:25 (Resomer RG 752) and d,l-PLA (resomer RG 206), and from Birmingham Polymers (Birmingham, Ala.). These copolymers are available in a wide range of molecular weights and ratios of lactic to glycolic acid.

In one embodiment, the coating comprises copolymers with desirable hydrophilic/hydrophobic interactions (see, e.g., U.S. Pat. No. 6,007,845, which describes nanoparticles and microparticles of non-linear hydrophilic-hydrophobic multiblock copolymers, which is incorporated by reference herein in its entirety). In a specific embodiment, the coating comprises ABA triblock copolymers consisting of biodegradable A blocks from PLG and hydrophilic B blocks from PEO.

5.1.4 Non-Polymeric Materials

The non-polymeric material suitable for use in the preparation of the particles and the drug eluting coatings of the present invention should be a material that is biocompatible and avoids irritation to body tissue. Preferably, the non-polymeric materials used in the particles and coating compositions of the present invention are selected from the following: sterols such as cholesterol, stigmasterol, beta-sitosterol, and estradiol; cholesteryl esters such as cholesteryl stearate; $C_{12}$-$C_{24}$ fatty acids such as lauric acid, myristic acid, palmitic acid, stearic acid, arachidic acid, behenic acid, and lignoceric acid; $C_{18}$-$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; spingomyelins such as stearyl, palmitoyl, and tricosanyl spingomyelins; ceramides such as stearyl and palmitoyl ceramides; glycosphingolipids; lanolin and lanolin alcohols; and combinations and mixtures thereof. Preferred non-polymeric materials include cholesterol, glyceryl monostearate, glycerol tristearate, stearic acid, stearic anhydride, glyceryl monooleate, glyceryl monolinoleate, and acetylated monoglycerides.

In certain embodiments, the non-polymeric material is hydrophilic. In a specific embodiment, the hydrophilic non-polymeric material comprises myristyl alcohol. In another specific embodiment, the hydrophilic non-polymeric material comprises carbon structures such as carbon tubes or balls, which can be made hydrophilic by attaching carboxylic acid groups by means of an acid treatment.

In certain other embodiments, the non-polymeric material is hydrophobic. In a specific embodiment, the hydrophobic non-polymeric material comprises cholesterol. In another specific embodiment, the hydrophobic non-polymeric material comprises liposomes.

In preferred embodiments, the non-polymeric materials can undergo forces, stress or mechanical challenges, e.g., expansion and contraction.

In preferred embodiments, the non-polymeric materials are biodegradable.

5.1.5 Types of Medical Device

Medical devices that are useful in the present invention can be made of any biocompatible material suitable for medical devices in general which include without limitation natural polymers, synthetic polymers, ceramics, and metallics. Metallic material (e.g., niobium, niobium-zirconium, and tantalum) is more preferable. Suitable metallic materials include metals and alloys based on titanium (such as nitinol, nickel titanium alloys, thermo-memory alloy materials), stainless steel, tantalum, nickel-chrome, or certain cobalt alloys including cobalt-chromium-nickel alloys such as Elgiloy® and Phynox®. Metallic materials also include clad composite filaments, such as those disclosed in WO 94/16646.

Metallic materials may be made into elongated members or wire-like elements and then woven to form a network of metal mesh. Polymer filaments may also be used together with the metallic elongated members or wire-like elements to form a network mesh. If the network is made of metal, the intersection may be welded, twisted, bent, glued, tied (with suture), heat sealed to one another; or connected in any manner known in the art.

The polymer(s) useful for forming the medical device should be ones that are biocompatible and avoid irritation to body tissue. They can be either biostable or bioabsorbable. Suitable polymeric materials include without limitation polyurethane and its copolymers, silicone and its copolymers, ethylene vinyl-acetate, polyethylene terephtalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

Other polymers that are useful as materials for medical devices include without limitation dacron polyester, poly (ethylene terephthalate), polycarbonate, polymethylmethacrylate, polypropylene, polyalkylene oxalates, polyvinylchloride, polyurethanes, polysiloxanes, nylons, poly(dimethyl siloxane), polycyanoacrylates, polyphosphazenes, poly(amino acids), ethylene glycol I dimethacrylate, poly(methyl methacrylate), poly(2-hydroxyethyl methacrylate), polytetrafluoroethylene poly(HEMA), polyhydroxylkanoates, polytetrafluorethylene, polycarbonate, poly(glycolide-lactide) co-polymer, polylactic acid, poly($\epsilon$-caprolactone), poly($\beta$-hydroxybutyrate), polydioxanone, poly($\gamma$-ethyl glutamate), polyiminocarbonates, poly(ortho ester), polyanhydrides, alginate, dextran, chitin, cotton, polyglycolic acid, polyurethane, or derivatized versions thereof, i.e., polymers which have been modified to include, for example, attachment sites or cross-linking groups, e.g., Arg-Gly-Asp (RGD), in which the polymers retain their structural integrity while allowing for attachment of molecules, such as proteins, nucleic acids, and the like.

The polymers may be dried to increase its mechanical strength. The polymers may then be used as the base material to form a whole or part of the medical device.

Furthermore, although the invention can be practiced by using a single type of polymer to form the medical device, various combinations of polymers can be employed. The appropriate mixture of polymers can be coordinated to produce desired effects when incorporated into a medical device.

The particles of the invention may also be used to form a medical or prosthetic device, preferably a stent, which may be inserted or implanted in a subject. In one embodiment, the particles of the invention may be incorporated into the base material needed to make the device. For example, in stent comprising a sidewall of elongated members or wire-like elements, the particles can be used to form the elongated members or wire-like elements.

In certain preferred embodiments, the particles described in Section 5.1.1 supra. are mixed with a polymer. Such mixture can be used to form a medical device or portions thereof. In specific embodiments, the particles and/or coating compositions comprising the particles constitute at least 5%, at least 10%, at least 20%, at least 30%, at least 40%, at least 50%, at least 60%, at least 70%, at least 80%, at least 90%, at least 95%, at least 97%, at least 99% or more by weight of the polymeric compositions used to form the medical device.

Examples of the medical devices suitable for the present invention include, but are not limited to, stents, surgical staples, catheters (e.g., central venous catheters and arterial catheters), guidewires, cannulas, cardiac pacemaker leads or lead tips, cardiac defibrillator leads or lead tips, implantable vascular access ports, blood storage bags, blood tubing, vascular or other grafts, intra-aortic balloon pumps, heart valves, cardiovascular sutures, total artificial hearts and ventricular assist pumps, and extra-corporeal devices such as blood oxygenators, blood filters, hemodialysis units, hemoperfusion units and plasmapheresis units. In a preferred embodiment, the medical device is a stent.

Medical devices of the present invention include those that have a tubular or cylindrical-like portion. The tubular portion of the medical device need not to be completely cylindrical. For instance, the cross-section of the tubular portion can be any shape, such as rectangle, a triangle, etc., not just a circle. Such devices include, without limitation, stents and grafts. A bifurcated stent is also included among the medical devices which can be fabricated by the method of the present invention.

Medical devices which are particularly suitable for the present invention include any kind of stent for medical purposes which is known to the skilled artisan. Suitable stents include, for example, vascular stents such as self-expanding stents and balloon expandable stents. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 5,449,373 issued to Pinchasik et al.

5.1.6 Methods of Coating the Medical Device

In the present invention, a coating composition comprising the particles as described in Section 5.1.2 supra. can be applied by any method to a surface of a medical device to form a coating. Examples of suitable methods are spraying, laminating, pressing, brushing, swabbing, dipping, rolling, electrostatic deposition and all modern chemical ways of immobilization of bio-molecules to surfaces. Preferably, the coating composition is applied to a surface of a medical device by spraying, rolling, laminating, and pressing. In one embodiment of the present invention, more than one coating methods can be used to make a medical device.

Furthermore, before applying the coating composition, the surface of the medical device is optionally subjected to a pre-treatment, such as roughening, oxidizing, sputtering, plasma-deposition or priming in embodiments where the surface to be coated does not comprise depressions. Sputtering is a deposition of atoms on the surface by removing the atom from the cathode by positive ion bombardment through a gas discharge. Also, exposing the surface of the device to a primer is a possible method of pre-treatment.

In certain embodiments, the medical device of the present invention is covered with one coating layer. In certain other embodiments, the medical device of the present invention is covered with more than one coating layer. In preferred embodiments, the medical device is covered with different coating layers. For example, the coating can comprise a first layer and a second layer that contain different biologically active materials. Alternatively, the first layer and the second layer may contain an identical biologically active material having different concentrations. In one embodiment, either the first layer or the second layer may be free of biologically active material.

In another embodiment, the coating can comprise a first layer and a second layer that contain different therapeutic agents. Alternatively, the first layer and second layer may contain an identical therapeutic agent having different concentrations.

5.2 Therapeutic Uses

The invention relates generally to the therapeutic use of the particles, drug eluting coatings, and coated medical devices described in Sections 5.1.1., 5.1.2 and 5.1.6, respectively, to address conditions such as inhibiting cell proliferation, contraction, migration or hyperactivity in a subject. Pharmaceutical compositions, body implants, and medical devices comprising particles comprising therapeutic agents as described in Section 5.1.1 supra. can be injected, inserted or implanted into a subject in need thereof.

In certain embodiments, the therapeutic agent may be used to inhibit the proliferation, contraction, migration and/or hyperactivity of cells of the brain, neck, eye, mouth, throat, esophagus, chest, bone, ligament, cartilage, tendons, lung, colon, rectum, stomach, prostate, breast, ovaries, fallopian tubes, uterus, cervix, testicles or other reproductive organs, hair follicles, skin, diaphragm, thyroid, blood, muscles, bone, bone marrow, heart, lymph nodes, blood vessels, arteries, capillaries, large intestine, small intestine, kidney, liver, pancreas, brain, spinal cord, and the central nervous system. In a preferred embodiment, the therapeutic agent is useful for inhibiting the proliferation, contraction, migration and/or hyperactivity of muscle cells, e.g., smooth muscle cells.

In certain other embodiments, the therapeutic agent may be used to inhibit the proliferation, contraction, migration and/or hyperactivity of cells in body tissues, e.g., epithelial tissue, connective tissue, muscle tissue, and nerve tissue. Epithelial tissue covers or lines all body surfaces inside or outside the body. Examples of epithelial tissue include, but are not limited to, the skin, epithelium, dermis, and the mucosa and serosa that line the body cavity and internal organs, such as the heart, lung, liver, kidney, intestines, bladder, uterine, etc. Connective tissue is the most abundant and widely distributed of all tissues. Examples of connective tissue include, but are not limited to, vascular tissue (e.g., arteries, veins, capillaries), blood (e.g., red blood cells, platelets, white blood cells), lymph, fat, fibers, cartilage, ligaments, tendon, bone, teeth, omentum, peritoneum, mesentery, meniscus, conjunctiva, dura mater, umbilical cord, etc. Muscle tissue accounts for nearly one-third of the total body weight and consists of three distinct subtypes: striated (skeletal) muscle, smooth (visceral) muscle, and cardiac muscle. Examples of muscle tissue include, but are not limited to, myocardium (heart muscle), skeletal, intestinal wall, etc. The fourth primary type of tissue is nerve tissue. Nerve tissue is found in the brain, spinal cord, and accompanying nerve. Nerve tissue is composed of specialized cells called neurons (nerve cells) and neuroglial or glial cells.

In preferred embodiments, the particles comprise one or more therapeutic agents useful for inhibiting muscle cell proliferation, contraction, migration or hyperactivity.

The particles, drug eluting coatings, and coated medical devices of the present invention may also be used to treat diseases that may benefit from decreased cell proliferation, contraction, migration and/or hyperactivity.

In particular, the therapeutic agents, such as paclitaxel, may be used to treat or prevent diseases or conditions that may benefit from decreased or slowed cell proliferation, contraction, migration or hyperactivity. In specific embodiments, the present invention inhibits at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, at least 10%, at least 5%, or at least 1% of cell proliferation, contraction, migration and/or hyperactivity.

The present invention further provides methods for treating or preventing stenosis or restenosis. In particular, the invention relates to methods for treating or preventing stenosis or restenosis by inserting or implanting a medical device comprising the particles of the invention into a subject.

As used herein, the terms "subject" and "patient" are used interchangeably. The subject can be an animal, preferably a mammal including a non-primate (e.g., a cow, pig, horse, cat, dog, rat, and mouse) and a primate (e.g., a monkey, such as a cynomolgous monkey, chimpanzee, and a human), and more preferably a human.

In one embodiment, the subject can be a subject who had undergone a regimen of treatment (e.g., percutaneous transluminal coronary angioplasty (PTCA), also known as balloon angioplasty, and coronary artery bypass graft (CABG) operation).

The therapeutically effective amount of a therapeutic agent for the subject will vary with the subject treated and the therapeutic agent itself. The therapeutically effective amount will also vary with the condition to be treated and the severity of the condition to be treated. The dose, and perhaps the dose frequency, can also vary according to the age, gender, body weight, and response of the individual subject.

The present invention is useful alone or in combination with other treatment modalities. In certain embodiments, the subject can be receiving concurrently other therapies to treat or prevent stenosis or restenosis. In certain embodiments, the treatment of the present invention further includes the administration of one or more immunotherapeutic agents, such as antibodies and immunomodulators, which include, but are not limited to, HERCEPTIN®, RITUXAN®, OVAREX™, PANOREX®, BEC2, IMC-C225, VITAXIN™, CAMPATH® I/H, Smart MI95, LYMPHOCIDE™, Smart I D10, ONCOLYM™, rituximab, gemtuzumab, or trastuzumab. In certain other embodiments, the treatment method further comprises hormonal treatment. Hormonal therapeutic treatments comprise hormonal agonists, hormonal antagonists (e.g., flutamide, tamoxifen, leuprolide acetate (LUPRON™), LH-RH antagonists), inhibitors of hormone biosynthesis and processing, steroids (e.g., dexamethasone, retinoids, betamethasone, cortisol, cortisone, prednisone, dehydrotestosterone, glucocorticoids, mineralocorticoids, estrogen, testosterone, progestins), antigestagens (e.g., mifepristone, onapristone), and antiandrogens (e.g., cyproterone acetate).

In certain embodiments, the drug eluting coating is capable of providing sustained release of the therapeutic agents over a time period. The time period for release of a therapeutic agent from the coating ranges from 1 hour, 2 hours, 3 hours, 4 hours, 5 hours, 6 hours, 12 hours, 1 day, 2 days, 3 days, 4 days, 5 days, 6 days, 1 week, 2 weeks, 3 weeks, 1 month, 2 months, 3 months, 4 months, 5 months, 6 months, 1 year, 2 years, or longer. Preferably, the time period for release of the therapeutic agent from the coating ranges from 1 hour to 24 months.

6. EXAMPLES

6.1 Stents Coated with a Hydrophilic Coating that Release Taxol®

6.1.1 Materials and Methods

The hydrophobic therapeutic agent Taxol® (i.e., paclitaxel) is packaged inside nanosized shells that have a hydrophilic outer layer, a hydrophobic inner layer, and a core to form particles as described in Radtchenko et al. (*Int J Pharm.* 2002; 242: 219-23). The particles are then evenly dispersed in a biodegradable, hydrophilic polyvinyl alcohol (PVA) or poly (L-lactide) (PLLA) coating.

Stent A is covered with Taxol® PVA coating. Stent B is covered with Taxol® PLLA coating. Stent C is first covered with a ceramic layer and then covered with Taxol® PVA coating. Stent D is first covered with a ceramic layer and then covered with Taxol® PLLA coating.

The dissolution/absorption rate of the PVA or PLLA coating, and the release rate of Taxol® in each of the stents are measured in solutions and cell cultures.

6.1.2 Discussion

As the biodegradable PVA or PLLA coating dissolves in solutions or becomes absorbed by cells, the Taxol®-containing nanoparticles will be revealed one by one. As the outer layer of the nanoparticles itself begins to break down, the hydrophobic Taxol® content is released, which will then be rejected from the hydrophilic coating and forced into the surrounding solution or cells. In essence, the inventor has created a system which allows the release of Taxol® at a very defined rate with the additional benefit that hydrophilic coatings are more biocompatible than hydrophobic coatings.

Further, the inventor has extended the time period for releasing Taxol® from stents by covering the stent surface with a ceramic layer prior to covering it with the drug eluting coating.

7. EQUIVALENTS

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

What is claimed is:

1. A medical device comprising a surface and a coating disposed on the surface, wherein the coating comprises a first hydrophilic polymeric material incorporating a plurality of particles, and wherein the particles comprise an outer layer comprising a second hydrophilic polymeric material, an inner layer comprising a hydrophobic polymeric material, and a core comprising a hydrophobic therapeutic agent.

2. The medical device of claim 1, wherein the particles comprise nanoparticles.

3. The medical device of claim 1, wherein the first hydrophilic polymeric material is biodegradable.

4. The medical device of claim 1, wherein the first hydrophilic polymeric material comprises polyvinyl alcohol (PVA) or poly(L-lactide) (PLLA).

5. The medical device of claim 1, wherein the first and second hydrophilic polymeric materials are the same.

6. The medical device of claim 1, wherein the outer layer of the particles is biodegradable.

7. The medical device of claim 1, wherein the inner layer of the particles is biodegradable.

8. The medical device of claim 1, wherein the medical device is a stent.

9. The medical device of claim 1, wherein the coating is capable of providing sustained release of the therapeutic agent over a time period ranging from about 1 hour to about 2 years.

10. The medical device of claim 1, wherein the therapeutic agent inhibits cell proliferation, contraction, migration or hyperactivity.

11. The medical device of claim 1, wherein the therapeutic agent comprises paclitaxel.

12. The medical device of claim 1, wherein the surface comprises a ceramic layer.

13. A method for treating stenosis or restenosis comprising inserting or implanting the medical device of claim 1 into a subject.

14. A medical device comprising a surface and a coating disposed on the surface, wherein the coating comprises a first hydrophilic, biodegradable polymeric material incorporating a plurality of nanoparticles, and wherein the nanoparticles comprise an outer layer comprising a second hydrophilic polymeric material, an inner layer comprising a hydrophobic polymeric material, and a core comprising paclitaxel.

* * * * *